United States Patent [19]

De et al.

[11] Patent Number: 4,992,421
[45] Date of Patent: Feb. 12, 1991

[54] LUTEINIZING HORMONE RELEASING HORMONE ANTAGONIST

[75] Inventors: Biswanath De, Vernon Hills; Hwan-Soo Jae, Glencoe; Jacob J. Plattner, Libertyville, all of Ill.

[73] Assignee: Abbott Laboratories, Abbott Park, Ill.

[21] Appl. No.: 183,201

[22] Filed: Apr. 19, 1988

[51] Int. Cl.$^5$ ............... A61K 37/02; C07K 5/06; C07K 5/08
[52] U.S. Cl. ........................ 514/19; 514/18; 548/204; 548/214; 548/236; 548/247; 548/249; 548/266.2; 548/266.4; 548/336; 530/331
[58] Field of Search ............ 548/336, 204, 214, 236, 548/247, 249, 266.2, 266.4; 514/19

[56]     References Cited
         U.S. PATENT DOCUMENTS

| 4,002,738 | 1/1977 | Johnson et al. | 424/177 |
| 4,005,194 | 1/1977 | Johnson | 424/177 |
| 4,335,125 | 6/1982 | Heeres et al. | 424/250 |

OTHER PUBLICATIONS

J. Trachtenberg et al., Lancet, 2, 433, (1984), "Ketoconazole Therapy for Advanced Prostate Cancer".
A. Pont et al., Clin. Res., 31 91A, (1983), "Effect of High Dose Ketoconazole on Adrenal and Testicular Function".
A. Pont et al., Clin. Res., 30 99A, (1982), "Ketoconazole Inhibits Adrenal Steroid Synthesis".
J. Trachtenberg et al., J. of Urology, 130 152, (1983), "Ketoconazole: A Novel and Rapid Treatment for Advanced Prostatic Cancer".
A. Pont et al., Annals of Inter. Med., 97 370, (1982), "Ketoconazole Blocks Adrenal Steroid Synthesis".
A. Pont et al., Arch. Intern. Med., 142 2137, (1982), "Ketoconazole Blocks Testosterone Systhesis".

*Primary Examiner*—Mukund J. Shah
*Assistant Examiner*—Philip I. Datlow
*Attorney, Agent, or Firm*—Steven R. Crowley

[57]     ABSTRACT

The present invention relates to novel luteinizing hormone releasing hormone antagonists

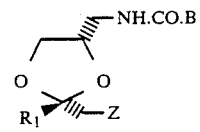

The invention also relates to pharmaceutical compositions containing such compounds and to the use of such compounds for suppressing levels of sex hormones in male or female mammals.

8 Claims, No Drawings

LUTEINIZING HORMONE RELEASING HORMONE ANTAGONIST

TECHNICAL FIELD

This invention relates to a series of novel LHRH antagonist compounds as well as to compositions containing the new antagonist compounds. The invention also relates to the use of such compounds for suppressing levels of sex hormones in male or female mammals.

BACKGROUND OF THE INVENTION

Luteinizing Hormone Releasing Hormone, known as LHRH or GnRH, is a decapeptide that is produced in the hypothalamus and binds to a receptor on the pituitary gland causing the release of Luteinizing Hormone (LH) and Follicle-Stimulating Hormone (FSH) from the pituitary. Subsequently, LH and FSH act on the gonads to stimulate the synthesis of steroid sex hormones. The pulsatile release of LHRH, and thereby the release of LH and FSH, controls the reproductive cycle in domestic animals and humans.

Acute doses of LHRH agonists increase the levels of LH and steroid sex hormones in both animals and humans. Paradoxically, chronic doses of these agonists suppress the levels of LH and steroid hormones resulting in an inhibition of the pituitary-gonadal axis characterized by a decrease of the levels of sex steroids and the atrophy of accessory sex organs. The same effect is observed in both animals and humans after administration of acute or chronic doses of LHRH antagonists. LHRH agonists are currently used, or are under clinical investigation, for the treatment of several hormone dependent diseases such as prostate cancer, prostatic hypertrophy, endometriosis, uterine fibroids, precocious puberty, and breast cancer. They also have been used as contraceptives. For a review of LHRH analogs see J. Sandow, et al., "Hypothalamic Hormones, Chemistry, Physiology, and Clinical Applications", edited by D. Gupta and W. Voeters, p. 307 (1978).

The discovery of gonadal steroid suppression produced by an LHRH agonist led to the successful development of clinical therapeutic agents such as leuprolide, U.S. Pat. No. 4,005,063, for use in the treatment of hormone-dependent breast and prostate cancer. However, to produce an agonistic response through a receptor-substrate complex, the molecule must meet the geometrical constraints of the receptor pocket and also meet the electronic requirements of the environment. This is particularly true where the substrate happens to be a long-chain polypeptide molecule. Many LHRH agonists have been made, but no agonist of less than eight amino acids in length has shown appreciable potency. Further, these agonist compounds are not appropriate for oral administration because they lack oral activity. For example, leuprolide is less than 1% bioavailable from the duodenum. Further, the mechanism by which these agonists induce the pituitary to release large amounts of LH during the first few weeks of the desensitization period also produces undesirable side effects, which include nausea, diarrhea, hot flashes, bone pain, urinary tract obstruction, and in some cases neurological problems. Manni, et al., Endocrine Rev., 7, 89–94 (1986).

An LHRH antagonist would avoid the unpleasant side effects accompanying the initial surge of LH which follows the administration of an LHRH agonist. Therefore, it is desirable to prepare an LHRH antagonist which will suppress steroid production by blocking LH-release. LHRH agonists work through a desensitization mechanism, while LHRH antagonists block the LHRH receptor by a competitive binding mechanism.

LHRH analogs have been shown to be effective by intravenous, subcutaneous or depot administration. Intranasal and intravaginal administration are effective only at very high doses. Currently known LHRH antagonists are not orally active, showing 0.1% to 1% potency following oral administration when compared to intravenous doses, and are effective only at very high doses. This very low oral activity is due to the fact that the long peptide chain of an antagonist is readily metabolized by the enzymes that are present in the digestive system. It would, therefore, be desirable to prepare an antagonist that is stable against enzymatic degradation and that is active after oral administration in animals and humans.

The prior art includes the antifungal drug, ketoconazole, U.S. Pat. No. 4,335,125, which was found to inhibit testicular and adrenal steroid synthesis by blocking a variety of enzyme systems. See Pont, et al., Arch. Intern. Med., 142, 2137–2140 (1982); Pont, et al., Ann. Intern. Med., 97, 370–372 (1982); Pont. et al., Clin. Res., 31, 91(abstr.) (1983); Pont. et al., Clin. Res., 30, 99(abstr.) (1982); Trachtenberg, et al., J. Urol., 130, 152–153 (1983). When given orally to patients in high dosages, from 200 to 1200 mg daily, ketoconazole was found to produce a dose dependent suppression of serum testosterone. See Trachtenberg, et al., The Lancet. 2, 433–435 (1984).

It is an object of the present invention to provide a novel series of antagonists which will suppress steroid production by blocking LH-release.

It would be desirable to prepare a novel series of orally active LHRH antagonists that are stable against enzymes and are applicable to oral administration in mammals, including humans.

DISCLOSURE OF THE INVENTION

This invention relates to a series of novel LHRH antagonists which can be represented by the formula:

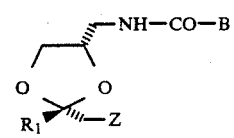

wherein Z is

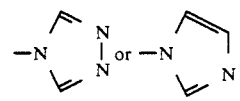

wherein $R_1$ is phenyl or substituted phenyl wherein the phenyl ring is substituted with one or two substituents independently selected from halogen, loweralkoxy, amino, loweralkylamino and $CH_3CONH-$; B is

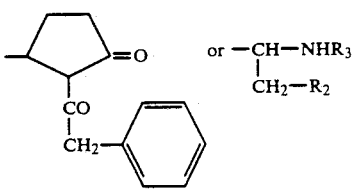

$R_2$ is selected from indolyl, imidazolyl, furyl, thienyl, pyrazolyl, oxazolyl, isoxazolyl, thiazolyl and isothiazolyl; $R_3$ is hydrogen, t-butyloxycarbonyl, benzyloxycarbonyl,

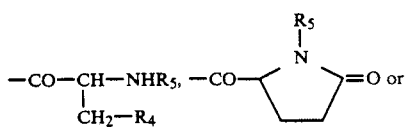 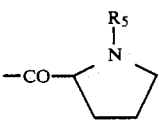

wherein $R_4$ is hydroxy, imidazolyl, furyl, thienyl, pyrazolyl, oxazolyl, isoxazolyl, thiazolyl or isothiazolyl; and wherein $R_5$ is hydrogen, t-butyloxycarbonyl (BOC), benzyloxycarbonyl (Cbz), —COCH(CH$_2$R$_6$)$_2$, —C(O)OCH$_2$CH(R$_6$)$_2$ wherein $R_6$ is phenyl;

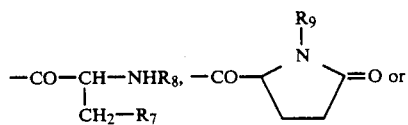 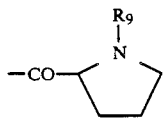

wherein $R_7$ is indolyl, 1-naphthyl, 2-naphthyl, phenyl, or substituted phenyl wherein the phenyl ring is monosubstituted with a substituent selected from hydroxy, methoxy, thiomethoxy and halogen; wherein $R_8$ is hydrogen, t-butyloxycarbonyl, benzyloxycarbonyl, —COCH(CH$_2$R$_{10}$)$_2$ or —C(O)OCH$_2$CH(R$_{10}$)$_2$ wherein $R_{10}$ is phenyl; and wherein $R_9$ is hydrogen, t-butyloxycarbonyl, benzyloxycarbonyl, —COCH(CH$_2$R$_{11}$)$_2$ or —COCH$_2$CH(R$_{11}$)$_2$ wherein $R_{11}$ is phenyl; or pharmaceutically acceptable salts thereof.

For convenience in describing this invention, the conventional abbreviations for the various common amino acids are used as generally accepted in the peptide art as recommended by the IUPAC-IUB commission on Biochemical Nomenclature, Biochemistry II, 1726 (1972). Other abbreviations which are useful in describing the invention are the following:

| Amino acids, protecting groups, reagents | Abbreviation |
|---|---|
| t-Butyloxycarbonyl | BOC |
| Benzyloxycarbonyl | Cbz |
| N,N'-Dicyclohexylcarbodiimide | DCC |
| Dimethylformamide | DMF |
| Ethyl | Et |
| Glutamic acid | Glu |
| Histidine | His |
| 1-Hydroxybenzotriazole | HOBt |
| Lithium aluminum hydride | LAH |
| Methyl | Me |
| Phenylalanine | Phe |
| Proline | Pro |
| Pyroglutamic acid | p-Glu |
| Serine | Ser |
| Tetrahydrofuran | THF |
| Tryptophan | Trp |
| 1-ethyl-3-(3'-dimethylamino)-propylcarbodiimide | EDAC |

The terms "halogen" or "halo" as used herein refer to chloro, bromo, fluoro, and iodo substituents.

The term "loweralkoxy" as used herein refers to straight or branched chain alkoxy radicals containing from 1 to 6 carbon atoms including but not limited to methoxy, ethoxy, propoxy, butoxy and the like.

The term "loweralkyl" as used herein refers to straight or branched chain saturated hydrocarbon groups having from 1 to 6 carbon atoms.

The term "loweralkylamino" as used herein refers to $R_{12}NH$— wherein $R_{12}$ is a loweralkyl radical containing from 1 to 6 carbon atoms including but not limited to methylamino, ethylamino, propylamino, butylamino and the like.

The compounds of the present invention can be used in the form of pharmaceutically acceptable salts derived from inorganic or organic acids. Included among such salts are the following: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptonate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate, and undecanoate. Also, the basic nitrogen-containing groups can be quarternized with such agents as loweralkyl halides, such as methyl, ethyl, propyl, and butyl chloride, bromides and iodides; dialkyl sulfates like dimethyl, diethyl, dibutyl, and diamyl sulfates; long chain halides such as decyl, lauryl, myristyl and stearyl chlorides, bromides and iodides, aralkyl halides like benzyl and phenethyl bromides and others.

Examples of acids which may be employed to form pharmaceutically acceptable acid addition salts include such inorganic acids as hydrochloric acid, sulphuric acid and phosphoric acid and such organic acids as oxalic acid, maleic acid, succinic acid and citric acid.

It has been found that compounds of the formula I and their physiologically acceptable salts have valuable pharmacological properties. The LHRH antagonist compounds of the invention are useful for treatment of diseases such as prostate cancer, prostatic hypertrophy, endometriosis, uterine fibroids, precocious puberty, breast cancer, acne, premenstrual syndrome, polycystic ovary syndrome and diseases which result from excessive gonadal hormone production in mammals, including humans. In particular, the compounds of the present invention are useful in the treatment of prostate cancers.

In the practice of the method of this invention, an effective amount of a compound of the invention or a pharmaceutical composition containing the same is administered to the subject in need of, or desiring, such treatment. The compounds or compositions of the present invention can be administered by any of a variety of routes depending upon the specific end use, for example, the compounds can be administered orally, parenterally, including subcutaneous, intramuscular and intravenous administration, vaginally, rectally, bucally, transdermally or intranasally. The most suitable route in any given case will depend upon the use, the particular active ingredient, the subject involved, and the judgment of the medical practitioner. The compound or composition can also be administered by means of slow-release, depot or implant formulations as described more fully herein.

In general, to suppress levels of sex hormones in male or female mammals for the uses herein above described, it is expedient to administer the active ingredient in amounts between about 0.01 and 10 mg/kg body weight per day, preferably between about 0.1 and 5.0 mg/kg body weight per day. This administration may be accomplished by a single daily administration, by distribution over several applications or by slow release in order to achieve the most effective results.

The exact dose and regime for administration of these compounds and compositions will necessarily be dependent upon the needs of the individual subject being treated, the type of treatment, the degree of affliction or need and, of course, the judgment of the medical practitioner. In general, parenteral administration requires a lowe dosage than other methods of administration which are more dependent upon absorption.

A further aspect of the present invention relates to pharmaceutical compositions containing as active ingredient a compound of the present invention. Such pharmaceutical compositions include the compounds of the present invention in admixture with a pharmaceutically acceptable, non-toxic carrier as employed for parenteral injection, for oral administration in solid or liquid form, for rectal administration and the like.

Compositions according to the invention for parenteral injection can comprise pharmaceutically acceptable sterile aqueous or nonaqueous solutions, suspensions or emulsions. The sterile injectable preparation can be a sterile injectable solution or a solution in a nontoxic parenterally acceptable diluent or solvent, for example, as a solution in 1,3-butanediol. Among the acceptable vehicles and solvents that can be employed are water, Ringer's solution and isotonic sodium chloride solution. Examples of suitable nonaqueous carriers, diluents, solvents or vehicles include propylene glycol, polyethylene glycol, vegetable oils, such as olive oil, and injectable organic esters such as ethyl oleate. Such compositions can also contain adjuvants such as preserving, wetting, emulsifying, and dispersing agents. They can also be manufactured in the form of sterile solid compositions which can be dissolved in sterile water, or some other sterile injectable medium immediately before use.

Solid dosage forms for oral administration include capsules, tablets, pills, powders and granules. In such solid dosage forms, the active compound is admixed with at least one inert diluent such as sucrose, lactose or starch. Such dosage forms can also comprise, as is normal practice, additional substances other than diluents, e.g., lubricating agents such as magnesium stearate. In the case of capsules, tablets and pills, the dosage forms can also comprise buffering agents. Tablets and pills can additionally be prepared with enteric coatings.

Liquid dosage forms for oral administration include pharmaceutically acceptable emulsions, solutions, suspensions, syrups and elixirs containing inert diluents commonly used in the art, such as water. Besides such inert diluents, compositions can also include adjuvants, such as wetting agents, emulsifying and suspending agents, and sweetening, flavoring and perfuming agents.

Sustained or directed release compositions can be formulated, for example, by encapsulation in a slow degrading nontoxic non-antigenic polymer such as a polylactic acid/polyglycolic acid polymer, as described in U.S. Pat. No. 3,773,919. The active compound can be protected with differentially degradable coatings, such as by microencapsulation multiple coatings. Additionally, a dosage form can contain a pharmaceutically acceptable non-toxic salt of a compound of the invention which has a low degree of solubility in body fluids. Additional slow release, depot or implant formulations, e.g. liposomes, are well known in the literature. See, for example, Sustained and Controlled Release Drug Delivery Systems, J. R. Robinson ed., Marcel Dekker, Inc., New York (1978).

Compositions for rectal administration are preferably suppositories which can contain, in addition to the active substance, a suitable nonirritating excipient such as cocoa butter, suppository wax, or polyethylene glycols which are solid at ordinary temperatures but liquid at the rectal temperature and will, therefore, melt in the rectum and release the LHRH antagonist.

It will be understood, however, that actual dosage levels of active ingredients in the compositions of the invention can be varied so as to obtain an amount of active ingredient effective to achieve LHRH antagonist activity in accordance with the desired method of administration. It will be appreciated that the actual preferred amounts of active compound in a specific case will vary according to the specific compound being utilized. Further, the selected dosage level depends upon the route of administration, the desired duration of treatment and other factors.

Compounds according to this invention can be prepared by coupling an acid of the formula II with an amine of the formula III as illustrated in the following reaction:

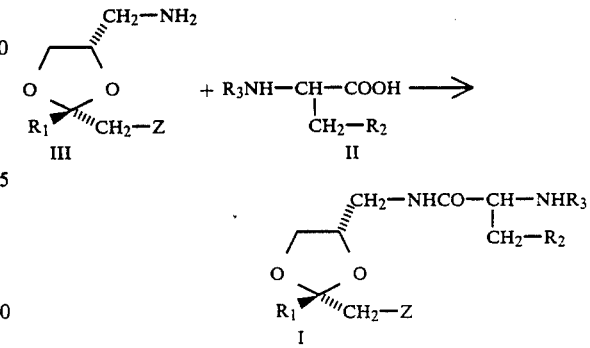

wherein Z as well as $R_1$, $R_2$, $R_3$, etc. are the same as described above.

The amine III can be prepared from a ketal alcohol (1), as illustrated in the following reaction scheme. The ketal alcohol can be synthesized following the published method according to Heeres, et al., J. Med.

Chem., 22, 1003–1005 (1979). For example, ketalization of 2,4-dichloroacetophenone with glycerine can be performed in a benzene-1-butanol medium with azeotropic removal of water in the presence of a catalytic amount of p-toluenesulfonic acid.

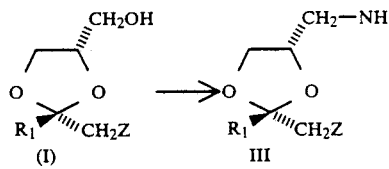

wherein Z as well as $R_1$, $R_2$, $R_3$, etc. are the same as described above.

The amino acid II can be prepared using standard amino acid or peptide chemistry.

The amino acid II is then coupled to the amine III utilizing conventional coupling procedures. For example, a mixed anhydride coupling method can be utilized wherein the reaction takes place in the presence of N-methylmorpholine and isobutyl chloroformate in either THF or $CH_2Cl_2$ at from 0 degrees C. to room temperature. Alternatively, an EDAC coupling method can be utilized wherein N-methylmorpholine is added to a solution containing the amine III, EDAC, HOBt, and the acid II in dry DMF at approximately −20 degrees C. The reaction mixture is stirred at −20 degrees C. for approximately 2 hours and then at room temperature to allow the reaction to proceed to completion. Thereafter, the resulting LHRH antagonist I can be isolated, for example, by solvent extraction techniques that are well known in the art. The product I can be further purified by methods well known in the art, for example, by chromatographic purification.

The foregoing can be better understood from the following examples, which are presented for the purposes of illustration and are not intended to limit the scope of the inventive concepts. As used in the following examples, the references to compounds, such as (1), (2), (3), etc., and to substituents, such as $R_1$, $R_2$, $R_3$, etc., refer to the corresponding compounds and substituents in the foregoing reaction scheme and in formula I, II, and III.

EXAMPLE 1

Preparation of (11)

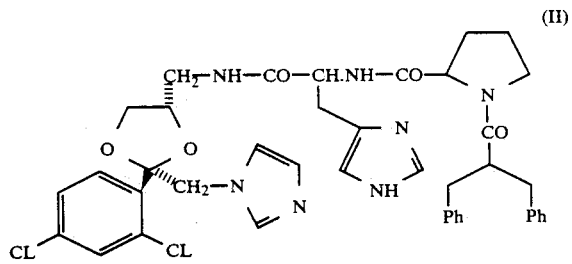

(a) Synthesis of amine (7)

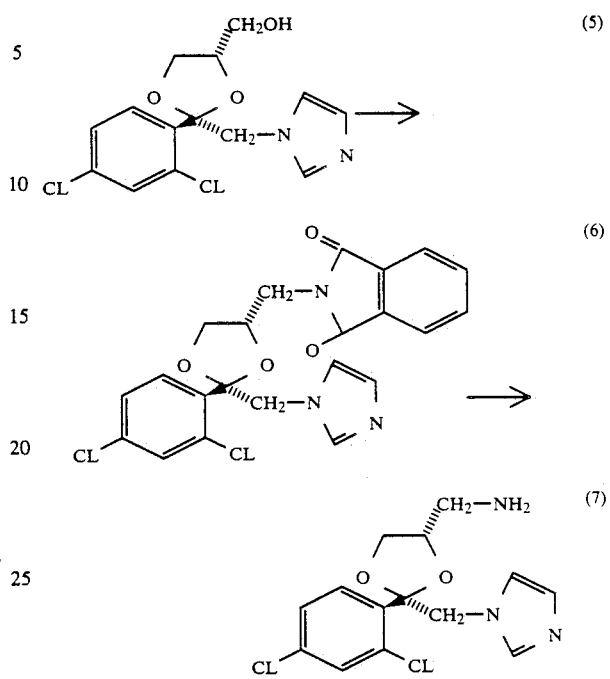

Under a nitrogen atmosphere, and at 0 degrees C., 1.26 mL (7.9 mmol) of diethyl azodicarboxylate was added to a solution of 2.50 g (7.60 mmol) of the alcohol (5), 2.10 g (8 mmol) triphenylphosphine, and 1.17 g (7.9 mmol) phthalimide in 60 mL of dry THF. The reaction was stirred at 0 degrees C. for 30 minutes, and then at room temperature for an additional 30 minutes. The solution was poured into a mixture of concentrated hydrochloric acid/AcOEt and allowed to separate. The aqueous layer was washed twice with AcOEt and basified with $Na_2CO_3$. The free base was extracted with AcOEt and crystallized from AcOEt/Hexane to yield 3.20 g. (92%) of the imide (6) as a white powder. $NH_3$-DCI-MS, m/z (relative intensity), 458 ($M^+$, 100%), $^1$H-NMR (DMSO-$d_6$, 300 MHz) 7.92–7.83 (m, 5H), 7.65 (d, H, J=1 Hz), 7.47 (d, H, J=9 Hz), 7.39 (dd, H, J=9 Hz, 1 Hz), 7.00 (bs, H), 6.70 (bs, H), 4.56 (d, H, J=15 Hz), 4.47 (d, H, J=15 Hz), 4.21 (m, H), 3.79 (dd, H, J=6 Hz, 7 Hz), 3.64 (dd, H, J=15 Hz, 5 Hz), 5.05–4.45 (m, 2H); Anal. ($C_{22}H_{17}O_4Cl_2N_3 \cdot \frac{1}{4}H_2O$) C,H,N.

To a solution of 60 mL of EtOH and 20 ml of THF was added 4.58 g (10 mmol) of the imide (6) from step (a). The solution was heated at reflux with 1.2 mL (20 mmol) of $NH_2$—$NH_2 \cdot H_2O$ for 3 hours. Thereafter, the reaction was cooled and the solid was removed by filtration. The filtrate was concentrated under vacuum and converted to HCl salt. Crystallization of the crude salt from AcOEt gave 3.16 g (79%) of the amine (7). DCI—$NH_3$—MS, m/z (relative intensity), 328 ($M^+$, 100%), 255 (22%), 221 (20%), and 165 (50%); $^1$H-NMR (Free Base, $CDCl_3$, 300 MHz) 7.57 (d, H, J=8.5 Hz), 7.53 (s, H), 7.47 (d, H, J=1.5 Hz), 7.24 (dd, H, J=9 Hz, 1.5 Hz), 7.01 (s, H), 6.59 (d, H, J=0.5 Hz), 4.49 (d, H, J=15 Hz), 4.38 (d, H, J=15 Hz), 3.59 (H, m), 3.82 (H, t, J=7 Hz), 3.44 (H, t, J=7 Hz), 2.64 (dd, H, J=13 Hz, 4 Hz), 2.50 (dd, H, J=13 Hz, 6 Hz), and 1.35 (bs, 2H-$NH_2$).

(b) Synthesis of methyl ester (10)

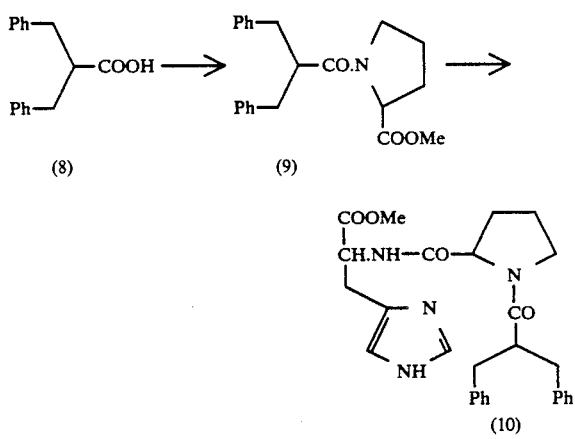

To a rapidly stirring solution of 2.4 g (10 mmol) of dibenzyl acetic acid (8) in 100 mL of benzene at room temperature was added 2.92 mL (4 equiv.) of thionyl chloride. The reaction was then refluxed for 14 hours. Thereafter, the solvent was removed under reduced pressure and 2.1 g (80% yield) of chloride intermediate was obtained. The chloride intermediate was coupled to 0.7 g (4.23 mmol) of L-proline methyl ester in 15 mL of $CH_2Cl_2$ at room temperature and in the presence of 590 uL (1 equiv.) of triethyl amine. The reaction was stirred at room temperature for 3 hours and then poured onto AcOEt/aqueous $NaHCO_3$. The organic layer was extracted, dried over $MgSO_4$ and concentrated under vacuum. Chromatographic purification of the crude product gave 1.25 g (85%) of the protected methyl ester (9).

To a solution of 3.42 mL of 2M LiOH in 8 mL of MeOH was added 1.2 g (3.42 mmol) of the methyl ester (9). The reaction mixture was stirred at room temperature for 3 hours. Thereafter, 7 mL of 1N HCl solution was added to the reaction mixture and a crude acid was extracted with AcOEt.

To a solution of 0.72 g (2.97 mmol) of L-His-OMe. 2 HCl, 1.20 g (3 equiv.) HOBt, 0.57 g (1 equiv.) EDAC, and 0.32 mL (2 equiv.) N-methyl morpholine in 15 mL DMF was added 1 g (2.97 mmol) of the above crude acid. The reaction was initially stirred at −20 degrees C. for 2 hours and then at room temperature overnight. The next day, the reaction mixture was poured onto a slurry of $CH_2Cl_2$/aqueous $NaHCO_3$. The organic layer was washed with brine, dried over $MgSO_4$ and concentrated under vacuum. Chromatographic purification (silica gel. $CH_2Cl_2$-MeOH) yielded 1.10 g (81%) of the ester (10).

(c) Hydrolysis of methyl ester (10)

At room temperature, 1 g (2.05 mmol) of the ester (10) was hydrolyzed with 4.1 mL (1N aqueous solution) of LiOH in 15 mL of MeOH for 3 hours. The salt was neutralized with 0.9 mL (4.55M solution) of HCl-Dioxane. The solvent was removed under reduced pressure and the acid thus obtained was used for the following coupling reaction.

(d) Coupling reaction

To a solution of 630 mg (1.58 mmol) of the amine (7) hydrochloride, 640 mg (3 equiv.) HOBt, 303 mg (1 equiv.) EDAC. and 0.35 mL (2 equiv.) N-methyl morpholine in 15 mL DMF was added 750 mg (1.58 mmol) of the acid from the foregoing step. The reaction mixture was stirred at −20 degrees C. for 2 hours and then at room temperature overnight. The crude reaction mixture was poured onto $CH_2Cl_2$/aqueous $NaHCO_3$. The organic layer was washed with brine, dried over $MgSO_4$ before being concentrated under vacuum. Chromatographic purification (silica gel, $CH_2Cl_2$-MeOH, the diastereomers were not separated) yielded 0.9 g (72%) of the product (11). FAB-MS, m/z (relative intensity), 784 (M+1, 60%); $^1$H-NMR ($CDCl_3$, 300 MHz) 7.62–7.43 (m, 4H), 7.38–7.08 (m, 15H), 4.47 (m, 2H), 4.26 (m. 1H), 4.10 (m, 1H), 4.74 (m, 1H), 3.60 (m, 1H), 3.45 (dd, 1H, J=6.0 Hz). 3.23 (m, 1H), 3.17–2.55 (m, 1OH), 1.92 (m, 2H), 1.68 (m, 2H), 1.41 (m, 2H); Anal. ($C_{41}H_{43}Cl_2N_7O_6 \cdot 2H_2O$) C,H,N.

EXAMPLE 2

Preparation of (15)

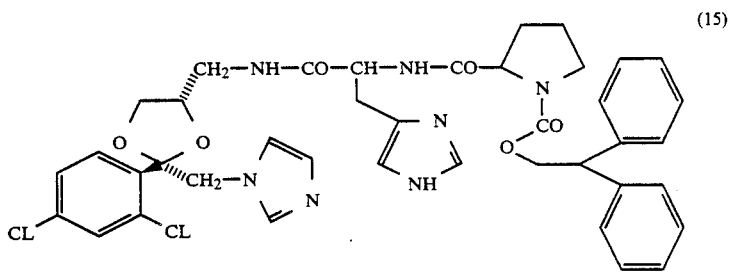

(a) Synthesis of 2,2-diphenyl-ethyl chloroformate (13)

To a rapidly stirring solution of 8.5 g (40 mmol) diphenyl acetic acid in 100 mL dry THF, at room temperature, was added 3.04 g (80 mmol) of LAH. The suspension was stirred at room temperature for 1 hour and then cooled to 0 degrees C. The excess LAH was decomposed by slow addition of 10% NaOH (200 mL aqueous solution). The product was extracted with AcOEt, dried over $MgSO_4$ and concentrated under vacuum to yield 7.1 g (90%) of 2,2-diphenyl ethanol (12).

To a solution of 7.0 g (35.4 mmol) of the alcohol (12) in 50 mL toluene at 0 degrees C., was slowly added 100 mL phosgene in toluene (12.5% phosgene in toluene). The reaction mixture was stirred at 0 degrees C. for 30 minutes and then at room temperature for 2 hours. The excess reagent and solvent was removed under reduced pressure and the crude product was quickly passed through a pad of silica gel (silica gel, $CH_2Cl_2$-Hexane 2:3) to yield 7.8 g (80%) of the chloroformate (13). DCI-$NH_3$-MS, m/z (relative intensity), 259 (M+, 55);

$^1$H-NMR (CDCl$_3$, 300 MHz) 7.28 (m, 10H), 4.83 (d, 2H, J=7.5 Hz), and 4.45 (t, 1H, J=7.5 Hz).

(b) Coupling reactions

L-proline methyl ester was coupled to 2,2-diphenylethyl chloroformate (13) following the procedure described in Example 1 to form the methyl ester (14). As described in Example 1, the methyl ester (14) was thereafter hydrolyzed with LiOH in MeOH to form the corresponding salt. The salt was neutralized with HCl-Dioxane and the acid thus obtained was used for the coupling reaction with the amine (7) hydrochloride as described in the coupling procedure (d) of Example 1 to provide the desired compound (15). FAB-MS, m/z (relative intensity), 786 (M+1. 100%); $^1$H-NMR (CDCl$_3$, 300 MHz) 7.53 (t, 2H, J=9.1 Hz), 7.47–7.03 (m, 16H). 7.00 (d. 1H, J=12 Hz), 6.75 (d, 1H, J=13.4 Hz), 4.70 (m, 1H). 4.55–3.96 (m, 6H), 3.68 (m, 1H), 3.60–3.12 (m. 5H). 3.08–2.8 (m, 2H), 2.18–1.72 (m, 6H); Anal. (C$_{40}$H$_{41}$Cl$_2$N$_7$O$_6$.2CF$_3$CO$_2$H .2H$_2$O) C,H,N.

EXAMPLE 3

Preparation of (16)

EXAMPLE 4

Preparation of (17)

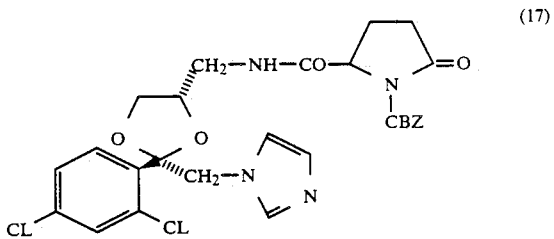

Using the amine (7) coupling procedure of Example 1, but replacing the acid derived from (10) with Cbz-p-Glu-OH gave the desired compound (17). DCI-NH$_3$, m/z (relative intensity), 573 (M$^+$, 30%), 465 (100%); $^1$H-NMR (DMSO-d$_6$, 300 MHz) 8.30 (m, H), 7.68 (dd, H, J=4 Hz, 2 Hz), 7.50–7.20 (m, 8H), 7.02 (bs, H), 6.82 (bs, H), 5.19 (d, H, J=13 Hz), 5.12 (d, H, J=13 Hz), 4.58 (m, H), 4.50 (d, 2H, J=4 Hz), 3.90 (m, H), 3.60 (m, H), 3.40 (m, H), 3.10 (m, H), 2.82 (m, H), 2.41 (m, H),

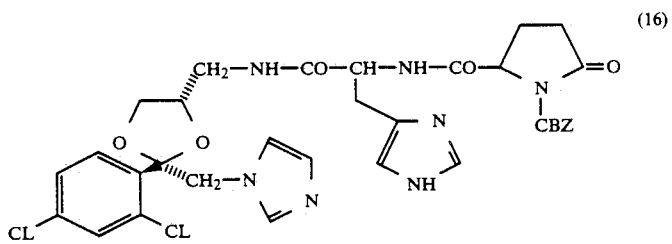

To a solution containing the 190 mg (0.58 mmol) of the amine (7) in 5 ml of DMF at 0 degrees C. was added 231 mg (0.58 mmol) of Cbz-p-Glu-His-OH, 143 mg (0.78 mmol) of N-Hydroxy-5-norbornene-2,3-dicarboximide, and 143 mg (0.69 mmol) of DCC. The reaction was allowed to reach room temperature over a 5 hour period and then stirred at this temperature overnight. The mixture was poured onto a slurry of aqueous saturated NaHCO$_3$/AcOEt. The organic layer was washed with brine, dried over MgSO$_4$, and concentrated under vacuum. Chromatographic purification of the crude product yielded 162 mg (39%) of the product (16). FAB-MS, m/z (relative intensity), 710 (M$^+$, 65%), 307 (31%), 289 (18%), 154 (100%), 136 (95%); $^1$H-NMR (DMSO-d$_6$, 300 MHz) 8.55 (bd, H, J=7 Hz), 8.01 (m, H), 7.68 (d, H, J=1.5 Hz), 7.55–7.30 (M. 10 H), 7.02 (bs, H), 6.81 (bs, H), 6.78 (bd, H), 5.18 (d, H, J=12 Hz), 5.10 (d, H, J=12 Hz), 4.68 (dd, H, J=9 Hz. 3 Hz), 4.51–4.49 (m, 3H), 3.82 (m, H), 3.68–3.55 (m, 2H), 3.15–2.60 (m, 5H), 2.38 (m, 2H), 2.25 (m, H), and 1.80 (m, H).

2.29 (m, H), and 1.80 (m, H); Anal. (C$_{27}$H$_{26}$O$_6$N$_4$Cl$_2$) C,H,N.

EXAMPLE 5

Preparation of (18)

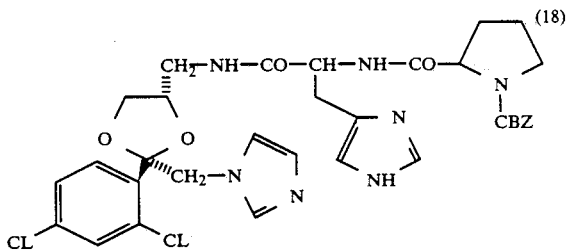

Using the amine (7) coupling procedure of Example 1, but replacing the acid derived from (10) with Cbz-Pro-His-OH gave the desired compound (18). FAB-MS, m/z (relative intensity), 696 (M+1, 100%); $^1$H-NMR (CDCl$_3$, 300 MHz) 7.65–7.03 (m, 12H), 7.0 (d, 1H, J=12 Hz), 6.79 (d, 1H, J=12 Hz), 5.15 (m, 2H). 4.52–4.24 (m, 4H), 4.04 (bs, 1H), 3.72 (m, 2H), 3.53 (m, 2H), 3.42–2.85 (m, 6H), 2.05 (m, 4H); Anal. (C$_{33}$H$_{35}$Cl$_2$N$_7$O$_6$.H$_2$O) C,H,N.

EXAMPLE 6

Preparation of (19)

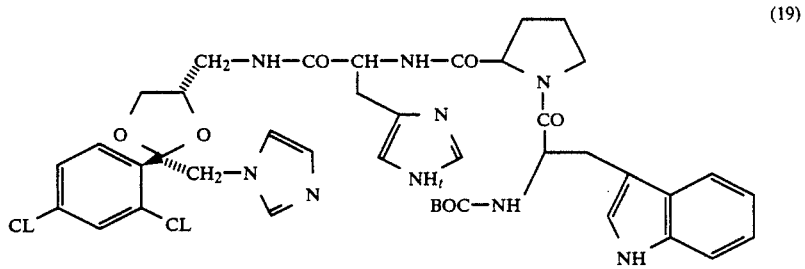
(19)

Using the amine (7) coupling procedure of Example 1, but replacing the acid derived from (10) with BOC-Trp-Pro-His-OH gave the desired compound (19). FAB-MS, m/z (relative intensity), 849 (M+1, 60%); $^1$H-NMR (CDCl$_3$, 300 MHz) 7.70–6.94 (m, 14H), 4.85 (m, 1H), 4.44 (m, 3H), 4.08 (bs, 1H), 3.72 (m, 2H), 3.43 (m, 2H), 3.25–2.25 (m, 9H), 2.15–1.60 (m, 9H), 1.43 (s, 9H); Anal. (C$_{41}$H$_{47}$Cl$_2$N$_9$O$_7$.2H$_2$O) C,H,N.

EXAMPLE 7

Preparation of (20)

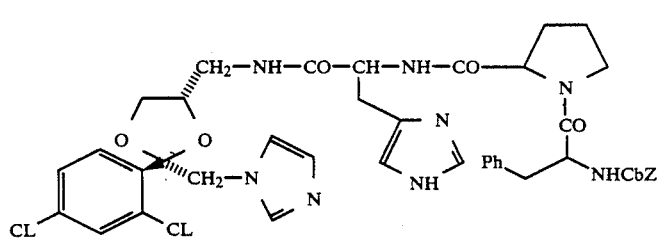
(20)

Using the amine (7) coupling procedure of Example 1, but replacing the acid derived from (10) with Cbz-Phe-Pro-His-OH gave the desired compound (20). FAB-MS, m/z (relative intensity), 843 (M+1, 100%); $^1$H-NMR (CDCl$_3$, 300 MHz) 8.0–7.06 (m, 17H), 7.03 (d, 1H, J=10.5 Hz), 6.84 (d, 1H, J=10.5 Hz), 5.06 (d, 2H, J=9.6 Hz), 4.78 (m, 1H), 4.58 (m, 1H), 4.42 (m, 4H), 4.1 (bs, 1H), 3.72 (m, 2H), 3.57–2.83 (m, 10H), 2.05 (m, 4H); Anal. (C$_{42}$H$_{44}$Cl$_2$N$_8$O$_7$. H$_2$O) C,H,N.

EXAMPLE 8

Preparation of (21)

(21)

Using the amine (7) coupling procedure of Example 1, but replacing the acid derived from (10) with L-Trp-OH gave the desired compound (21). FAB-MS, m/z (relative intensity) 514 (MH+, 55%), 185 (95%), 93 (100%); Anal. (C$_{25}$H$_{25}$N$_5$O$_3$Cl$_2$.2HCl.2H$_2$O) C, H, N.

EXAMPLE 9

Preparation of (22)

(22)
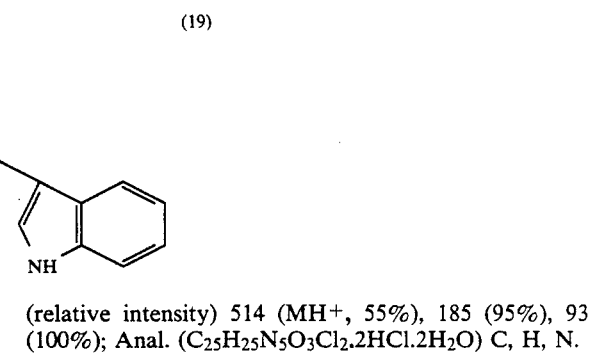

Using the amine (7) coupling procedure of Example 1, but replacing the acid derived from (10) with Ser-Trp-OH gave the desired compound (22). FAB-MS, m/z (relative intensity) 601 (M+H, 100%), 225 (55%), 185 (100%), 159 (45%); Anal. (C$_{28}$H$_{30}$N$_6$O$_5$Cl$_2$.3CF$_3$CO$_2$H) C, H, N.

EXAMPLE 10

Preparation of (23)

(23)
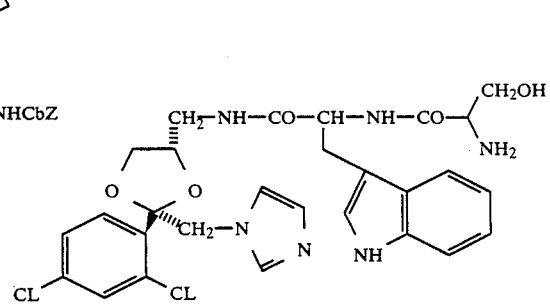

Using the amine (7) coupling procedure of Example 1, but replacing the acid derived from (10) with p-Glu- His-OH gave the desired compound (23). DCI-NH$_3$-MS, m/z (relative intensity), 576 (M+, 100%) and 281 (82%).

EXAMPLE 11

Preparation of (24)

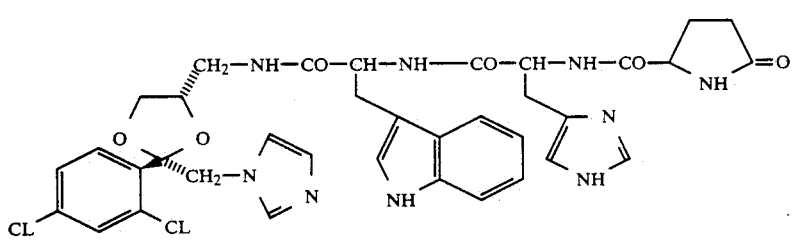

(24)

Using the amine (7) coupling procedure of Example 1, but replacing the acid derived from (10) with Cbz-p-Glu-His-Trp-OH gave the desired compound (24). FAB-MS, m/z (relative intensity), 762 (MH+, 100%), 728 (25%), 328 (15%) and 307 (25%).

ASSAY PROCEDURE

The biological activity of the compounds of the invention is determined by the following assay:

Receptor Binding. A radioligand receptor binding assay is performed in a similar way to that described in the literature (J. Marion et al., Mol. Pharmacol. 19 399 (1981)). [D-Leu$^6$-des Gly$^{10}$]-LHRH ethyl amide was radioiodinated by the chloramine-T method and used as the radioligand. Pituitary membranes containing LHRH receptors are prepared in batches from quick-frozen rat pituitaries obtained from Hilltop Labs. The radioligand (50 pM), receptors, and compounds to be tested are coincubated for 2 hours at 4° C. Bound ligand is separated from free ligand via centrifugation and aspiration. Compounds are tested at six half-log concentration increments, and the equilibrium dissociation constant (K$_I$) is calculated from the concentration which displaces 50% of specifically bound radioligand.

TABLE 1

| EXAMPLE No. | COMPOUND No. | LHRH RECEPTOR BINDING AFFINITY K$_I$ (uM) |
| --- | --- | --- |
| Example 1 | (11) | 1.14 |
| Example 2 | (15) | 0.48 |
| Example 3 | (16) | 1.90 |
| Example 4 | (17) | 31.00 |
| Example 5 | (18) | 1.12 |
| Example 6 | (19) | 0.50 |
| Example 7 | (20) | 0.97 |
| Example 8 | (21) | 10.00 |
| Example 9 | (22) | 4.78 |
| Example 10 | (23) | 10.00 |
| Example 11 | (24) | 2.00 |
| Ketoconazole | | 2.00 |

The foregoing is merely illustrative of the invention and is not intended to limit the invention to the disclosed compounds. Variations and changes which are obvious to one skilled in the art are intended to be within the scope and nature of the invention which are defined in the appended claims.

What is claimed is:

1. A compound of the formula:

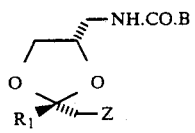

wherein Z is

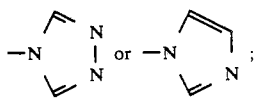

wherein R$_1$ is phenyl or substituted phenyl wherein the phenyl ring is substituted with one or two substituents independently selected from halogen, loweralkoxy, amino, loweralkylamino and CH$_3$CONH—; B is

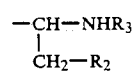

wherein R$_2$ is selected from indolyl, imidazolyl, furyl, thienyl, pyrazolyl, oxazolyl, isoxazolyl, thiazolyl and isothiazolyl; R$_3$ is

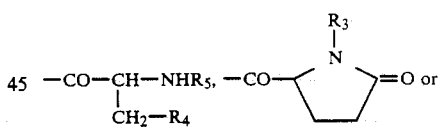

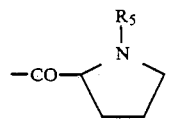

wherein R$_4$ is hydroxy, imidazolyl, furyl, thienyl, pyrazolyl, oxazolyl, isoxazolyl, thiazolyl or isothiazolyl and wherein R$_5$ is hydrogen, t-butyloxycarbonyl [(BOC)], benzyloxycarbonyl [(Cbz)], —COCH(CH$_2$R$_6$)$_2$ or —C(O)OCH$_2$CH(R$_6$)$_2$ wherein R$_6$ is phenyl; or a pharmeceutically acceptable salt thereof.

2. The compound of claim 1 wherein R$_1$ is 2,4-dichlorophenyl; Z is

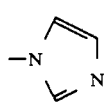

and B is

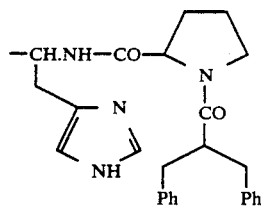

3. The compound of claim 1 wherein $R_1$ is 2,4-dichlorophenyl; Z is

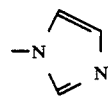

and B is

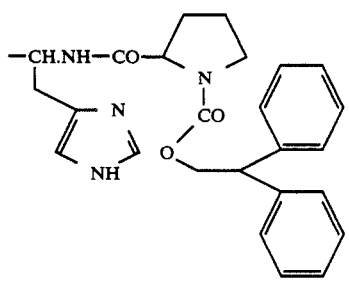

4. The compound of claim 1 wherein $R_1$ is 2,4-dichlorophenyl; Z is

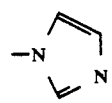

and B is

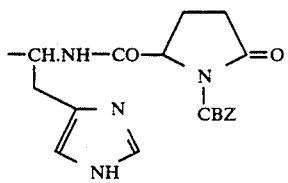

5. The compound of claim 1 wherein $R_1$ is 2,4-dichlorophenyl; Z is

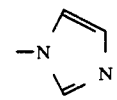

and B is

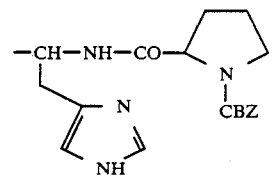

6. The compound of claim 1 wherein $R_1$ is 2,4-dichlorophenyl; Z is

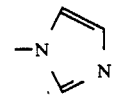

and B is

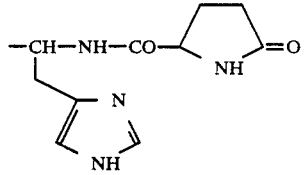

7. A method for suppressing levels of sex hormones in male or female mammals, comprising administering to a host in need of such treatment a therapeutically effective amount of a compound of claim 1.

8. A pharmaceutical composition for suppressing levels of sex hormones in female or male mammals, comprising a pharmaceutical carrier and a therapeutically effective amount of a compound of claim 1.

* * * * *

UNITED STATES PATENT AND TRADEMARK OFFICE
CERTIFICATE OF CORRECTION

PATENT NO. : 4,992,421

DATED : FEBRUARY 12, 1991

INVENTOR(S) : BISWANATH DE; HWAN-SOO JAE; JACOB J. PLATTNER.

It is certified that error appears in the above-identified patent and that said Letters Patent is hereby corrected as shown below:

On title page, Column 2, line 17, after "antagonists" add

--of the formula:--

Column 16, line 56, after "t-butyloxycarbonyl" delete --[(BOC)],--

Column 16, line 57, after "benzyloxycarbonyl" delete --[(Cbz)],--.

Signed and Sealed this

Twenty-first Day of July, 1992

Attest:

DOUGLAS B. COMER

Attesting Officer     Acting Commissioner of Patents and Trademarks